(12) United States Patent
Echeverri

(10) Patent No.: US 8,764,758 B2
(45) Date of Patent: Jul. 1, 2014

(54) ORIENTATION DEVICE FOR SURGICAL IMPLEMENT

(75) Inventor: Santiago Echeverri, Lausanne (CH)

(73) Assignee: San-tech Surgical Sàrl, Lausanne (CH)

( * ) Notice: Subject to any disclaimer, the term of this patent is extended or adjusted under 35 U.S.C. 154(b) by 914 days.

(21) Appl. No.: 10/565,002

(22) PCT Filed: Jul. 23, 2004

(86) PCT No.: PCT/CH2004/000466
§ 371 (c)(1),
(2), (4) Date: Jan. 19, 2006

(87) PCT Pub. No.: WO2005/009303
PCT Pub. Date: Feb. 3, 2005

(65) Prior Publication Data
US 2006/0184177 A1    Aug. 17, 2006

(30) Foreign Application Priority Data

Jul. 24, 2003   (WO) .................... PCT/CH03/00502

(51) Int. Cl.
| A61B 17/58 | (2006.01) |
| A61B 17/60 | (2006.01) |
| A61F 2/00 | (2006.01) |
| A61B 17/17 | (2006.01) |
| A61F 2/46 | (2006.01) |
| A61B 19/00 | (2006.01) |
| A61F 2/30 | (2006.01) |
| A61F 2/34 | (2006.01) |

(52) U.S. Cl.
CPC ......... *A61B 17/1746* (2013.01); *A61F 2/4609* (2013.01); *A61F 2002/4668* (2013.01); *A61B 2019/468* (2013.01); *A61F 2002/30538* (2013.01); *A61F 2/34* (2013.01); *A61F 2250/0006* (2013.01); *A61F 2002/4687* (2013.01); *A61F 2/4657* (2013.01)
USPC ............................................. 606/88; 606/99

(58) Field of Classification Search
USPC ............. 606/86, 99, 69, 87, 81, 96; 623/130; 408/16
See application file for complete search history.

(56) References Cited

U.S. PATENT DOCUMENTS 4,393,599 A * 7/1983 Sterrenberg .................... 33/336
4,893,619 A * 1/1990 Dale et al. ...................... 606/87

(Continued)

FOREIGN PATENT DOCUMENTS

| DE | 200 06 515 | 8/2000 |
| GB | 2 224 937 | 5/1990 |

(Continued)

OTHER PUBLICATIONS

Japanese Office Action mailed Sep. 14, 2010 from Japanese Patent Application No. 2006-520648, and its English translation.

*Primary Examiner* — Andrew Yang
(74) *Attorney, Agent, or Firm* — Nixon & Vanderhye P.C.

(57) ABSTRACT

Orientation device for surgical use includes a frame and a level device attached to the frame. The feature may be oriented with a reference such as the Antero Superior Iliac Spine, the acetabulum or the operating table to position the pelvis or the device. The level device is adapted to define a reference plane. The device thus allows precise orientation with respect to the pelvis through use of a reference plane.

21 Claims, 15 Drawing Sheets

(56) References Cited

U.S. PATENT DOCUMENTS

| | | | |
|---|---|---|---|
| 5,030,221 A | * | 7/1991 | Buechel et al. .................. 606/91 |
| 5,141,512 A | * | 8/1992 | Farmer et al. ................... 606/87 |
| 5,700,268 A | * | 12/1997 | Bertin ........................... 606/102 |
| 6,102,915 A | | 8/2000 | Bresler et al. |
| 6,302,890 B1 | | 10/2001 | Leone, Jr. |
| 6,375,395 B1 | * | 4/2002 | Heintzeman ................... 408/16 |
| 6,395,005 B1 | * | 5/2002 | Lovell ............................ 606/91 |
| 6,743,235 B2 | * | 6/2004 | Subba Rao ...................... 606/91 |

FOREIGN PATENT DOCUMENTS

| | | |
|---|---|---|
| WO | WO 97/29698 | 8/1997 |
| WO | WO 02/067784 | 9/2002 |
| WO | WO 02/071987 | 9/2002 |

* cited by examiner

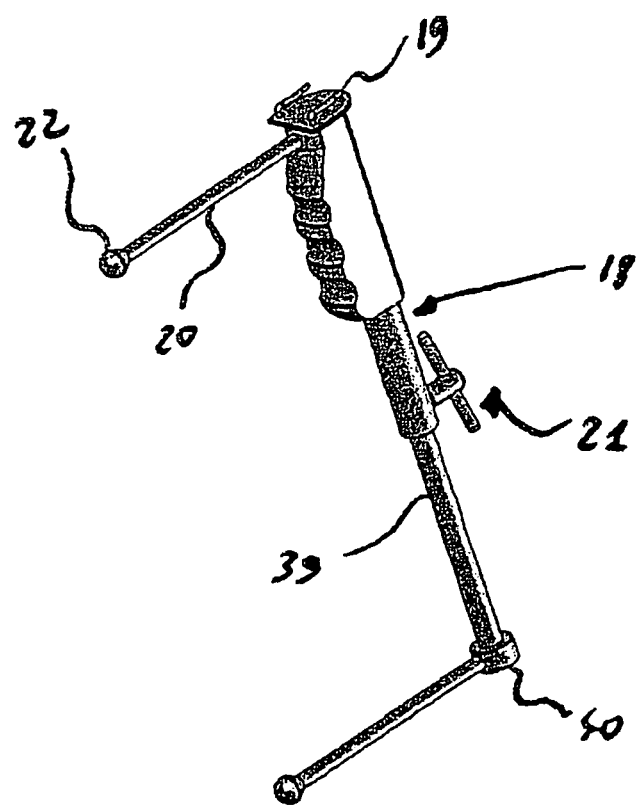

ORIENTATION DEVICE FOR SURGICAL IMPLEMENT

This application is the US national phase of international application PCT/CH2004/000466 filed 23 Jul. 2004 which designated the U.S. and claims benefit of PCT/CH03/00502, dated 24 Jul. 2003, the entire content of which is hereby incorporated by reference.

FIELD OF THE INVENTION

The invention relates to the field of surgical operations and in particular to methods and apparatuses for correctly positioning a surgical implement (a surgical tool, prosthesis or implant).

The invention is in particular, but not exclusively, useful for accurately aligning an acetabular prosthetic element.

BACKGROUND OF THE INVENTION

Improved orthopaedic procedures have made joint replacement common practice. In total hip arthroplasty, both the femoral or ball aspect of the joint as well as the acetabular or socket portion are replaced with prosthetic implants. Several patent and non-patent references exist in this field.

Orientation of the femoral stem is universally considered as less complex. Orientation of the acetabular component is far more complicated, and techniques designed to improve it are far less developed. Some of the present techniques are inadequate due to the complexity. The literature has shown a lack of accuracy even among experienced surgeons when estimating intraoperative orientation of the acetabular cup with standard techniques.

Some techniques developed for computer assisted surgery are promising but present limitations of their own and it may be some time before patients can benefit. Its world wide availability is limited due to high costs and special training required. There are several reasons for the lack of progress in this area. The orientation of the acetabular cup requires an adequate orientation of the pelvis in three planes. Its anatomy may be altered by disease, even severely altered in cases of revision arthroplasty. Present mechanical techniques use the floor level and the longitudinal axis of the operating table as a reference. Some devices use bubble levels, see e.g. U.S. Pat. No. 6,302,890, U.S. Pat. No. 5,700,268 or U.S. Pat. No. 5,122,145, the content of which are incorporated by reference herein, but they only provide an indication with respect to one direction (mono-axis). The initial position of the pelvis in three planes (Yaw, Roll and Pitch) is ignored and therefore can lead to errors. The initial position is also known to change significantly during the surgical intervention. The second problem with standard orientation devices is the assumption that the orientation of the pelvis in terms of flexion/extension is always the same with respect to the axis of the table. Additionally, standard mechanical orientation devices rely on visual references and therefore lack precision. In Minimally invasive surgery (MIS), small surgical incisions make it even more difficult to obtain adequate orientation of the components.

Many surgeons orient the acetabular component through subjective "feeling", a technique that has also been shown in the literature to be highly inaccurate and imprecise even in the most experienced hands. Studies in saw bone models comparing free hand techniques and standard mechanical orientation devices with computer assisted navigation have clearly shown the lack of accuracy and precision of both techniques. Lack of optimal orientation of both components acetabular cup and shaft as a couple, has been shown to result in limited range of motion due to impingement which leads to dislocation, early wear and loosening of the components.

The situation has lead to the use of imperfect techniques associated with prosthetic acetabular implantation, often involving the use of manually operated instrumentation which rely only on the surgeons hand and eye coordination to install the implant and occasionally relying on visual markers.

Studies have confirmed the importance of precise and matching positioning of both the acetabular and the femoral component. There is increasing awareness that improved reproducibility in component orientation fosters improved range of motion (before impingement of the implant to the cup prosthesis), implant longevity, reduced wear of the acetabular component and lower rates of dislocation.

Clinical epidemiology studies have extensively studied the sources of random errors (lack of precision) and systematic errors (lack of accuracy) for diagnostic or measuring tools such as the Gravity Assisted Navigation System in clinical practice. They have been divided into three aspects:
Observer variability
Subject variability (Differences among patients)
Instrument variability There is therefore a need for a simple to use and inexpensive instrumentation and techniques that can be applied to any type of hip prosthesis in either lateral or dorsal decubitus.

SUMMARY OF INVENTION

The objectives of the invention are achieved with a orientation device adapted for a surgical instrument made of a shaft having a distal end adapted to hold a surgical tool or prosthesis and a proximal end adapted to be held by a surgeon hand or by a robot arm.

The orientation device comprises:
instrument fixing means for fixing the orientation device to the instrument,
linear pointing means for pointing at least one reference point fixed to a patient, the reference point may be either an anatomical reference or a marker fixed to a specific part of the patient,
orientation means.

The orientation device is characterized by the fact that the orientation means are adapted to define a reference plane, i.e. the orientation means are of the dual-axis type, namely they allow the definition of the instrument orientation along two directions, defining thereby one plane. In the present case, the reference plane is perpendicular to the direction of the gravity force.

The orientation means may be adjustable, i.e. their orientation can be adapted according to the patient anatomy and/or the surgeon wishes. The adjustment can be made by any means commonly used, e.g. mechanical, electromechanical, etc....

Preferably the orientation device is a guide that can be easily released from the instrument so the instrument fixing means are adapted to allow a quick fixation or release of the orientation device to/from the instrument. The orientation device may be also permanently fixed to the instrument or be an instrument unto itself.

The linear pointing means may be made of a shaft with a free distal end adapted to aim at the reference point. The guide shaft is adapted to be parallel to the instrument shaft when the guide and instrument are fixed together. The plane defined by both shafts helps the surgeon to orientate the instrument when the guide shaft free end points towards the reference point.

The guide can be calibrated in order to use a particular anatomic reference point. The ASIS (Antero Superior Iliac Spine) being the preferred reference point that has been validated by the inventor using pelvic CT scans in patients to evaluate the morphologic variability.

In one embodiment of the invention, the guide shaft free end comprises two small parallel shafts oriented in a plane parallel to the plane defined by the instrument and guide shafts. The two small shafts act as a support for a surgeon finger in order to properly orientate the guide shaft with the reference point. More precisely, the surgeon finger forms a bridge between the guide free end and the reference point.

Instead of a shaft, the linear pointing means may be made of a laser beam.

In a preferred embodiment, the orientation means are of the electronic type. Such a system offers several advantages, in particular in computer assisted surgery where the level indication can be transmitted to a processing unit.

Alternatively the orientation means may be of the bubble or fluid type allowing thereby the use of a relatively inexpensive device.

In certain cases, the orientation device may have two orientation means, e.g. one for determining an orientation with a left hip and one for determining an orientation with a right hip.

In acetabular cup positioning, a pelvic positioner may be associated with the guide, the pelvic positioner comprising two feelers for contacting two distinct part of the pelvis and orientation means. The orientation means allow for strict positioning in lateral decubitus by assuring alignment of the feelers and hence the right and left ASIS with the vertical (direction of the force of gravity and the direction of the reaction to the force of gravity). In the case of a THR in dorsal decubitus, a positioner with three feelers can be used in order to align the anatomic plane of the pelvis defined by both ASIS and the pubis with respect to the vertical.

In another embodiment, an orientation device is used as a witness of pelvic orientation during surgery. The orientation witness comprises orientation means and fixing means for fixing the witness to the pelvis. Set to zero after aligning the pelvis in lateral or dorsal decubitus with the help of the pelvic positioner the orientation means allow to detect any change in pelvic position during the surgical intervention and to come back to the initial position at the time of cup orientation.

In another embodiment the guide also comprises an angle measuring device for measuring the angle between references points such as the ASIS (Antero Superior Iliac Spine) and the HJC (Hip Joint Center).

In acetabular cup alignment the method takes into consideration the adequate orientation of the pelvis to assure the desired position of the acetabular cup with respect to directions which are directly or indirectly derived from the direction of the force of gravity. The invention is characterized by the fact that, contrary to prior art devices which generally aid in the orientation of the hip, the invention allows precise orientation of the device with respect to the pelvis through use of a reference plane.

The method also permits measurement of the orientation of a cup that is already in place. This can be done by adapting the guide to the cup, and after aligning the pitch pointer to the ASIS, the level holder is bent setting the bubble to zero. It can then be adapted to a calibrating apparatus to measure the orientation both in abduction and anteversion. In an electronic device, it would be read off the dial.

The calibrating apparatus may comprise angle reproducing means for reproducing the angle at the ASIS between the pubis and the HJC as measured with the guide. In this case, the assembly made of the guide and the instrument preferably comprise an angle measuring device (goniometer) for measuring the said angle.

The instrument may be calibrated to assure a desired orientation depending on the design of the cup and the anteversion of the femoral stem or the specific pelvic flexion/extension of the patient. All this in order to obtain maximum impingement-free range of motion. This improves with simple means the accuracy and precision particularly of the acetabular cup that is lacking with present methods. A well known fact in clinical epidemiology states that any effort to improve precision improves accuracy.

The invention focuses on studying sources of error of acetabular orientation from a Clinical Epidemiology point of view in order to provide improved precision and accuracy by reducing instrument variability (See *Designing Clinical Research*, An Epidemiologic Approach, Hulley. Williams and Wilkins 1988).

Sources of Systematic Errors (Adapted to standard mechanical guides for cup orientation)
  Instrument Variability (guide used)
  Differences resulting from the instrument used.
    Eye coordination in two different planes
    Does not take into account pitch angle for axis of anteversion (but orientation of the table)
    Use of a mechanical guide that can not be calibrated with a gold standard.

Having identified the problem, the guide was created as a solution that complies with the standard strategies of clinical epidemiology for improving reliability of measuring instruments.

Strategies to increase precision (i.e., avoid random error, see *Designing Clinical Research*, An Epidemiologic Approach, Hulley. Williams and Wilkins 1988.)
  Standardising the methods for placement of the femoral and acetabular components by increasing objectivity.
  Training the surgeons in the standard techniques: Guide with Gravity Assisted Navigation System facilitates and improves training of surgeons.
  Improve patient positioning: Guide with Gravity Assisted Navigation System facilitates and improves patient positioning.
  Refining the instruments used for orientation of the components: making it easier to use allowing use by looking at it from different angles.
  Automating the instrument (avoid human error)
  Repeating the measurement
  Strategies to increase Accuracy (i.e., avoid bias; see again, *Designing Clinical Research*, An Epidemiologic Approach, Hulley. Williams and Wilkins 1988.)
  Standardising the methods in an operations manual.
  Training the surgeons in the standard (i.e reproducible) techniques.
  Improve patient positioning
  Refining the instruments used for orientation of the components.
  Automating the instruments
  Calibration of the instruments and the "position of the patient" (WITH A GOLD STANDARD)

DETAILED DESCRIPTION OF THE INVENTION

The invention will be discussed in a more detailed way here below. To this effect some examples, together with corresponding drawings, will be used.

FIG. 2 shows a pelvic positioner

LIST OF NUMERICAL REFERENCES

Figure 1A:
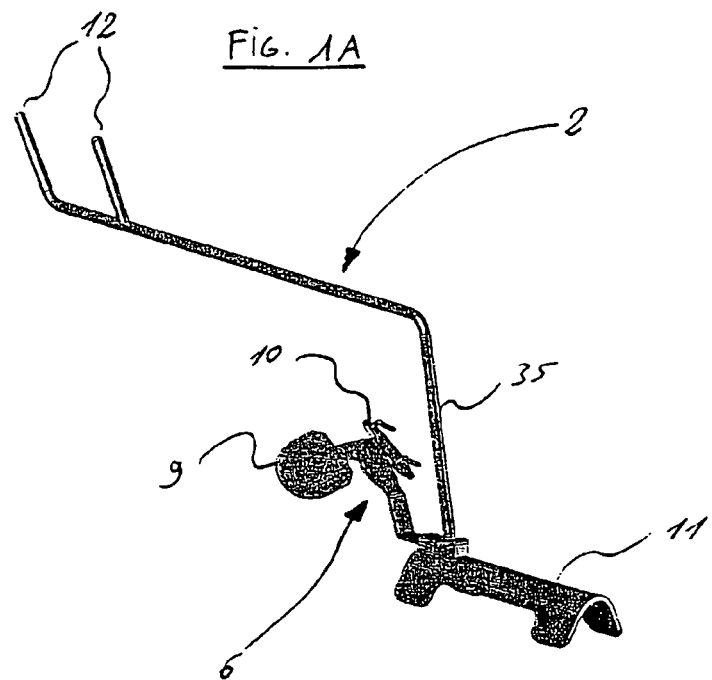
FIG. 1A shows an embodiment of a guide according to the invention.

1. Patient in strict lateral decubitus
2. Orientation device/guide
3. Orientation device/witness
4. Acetabular prosthetic cup instrument
5. Acetabulum
6. Guide bubble levels
7. ASIS
8. Guide shaft
9. Right indicator
10. Left indicator
11. Fixing means
12. Pointer
13. Pelvis/iliac crest
14. Prosthetic cup
15. Pelvic witness fixator/frame
16. Pelvic witness orientation means
17. Pelvic positioner
18. Support
19. Pelvic positioner orientation means
20. Bar
21. Length adjusting means
22. Pelvic feeler
Calibrating apparatus
24. Basis
25. Bubble level
26. Height adjusters
27. Scale for measuring anteversion mounted on a Gimbal mechanism
28. Calibration fork for right hip
29. Calibration fork for left hip
30. Axis of rotation for the anteversion
31. Scale for abduction
32. Axis of rotation for abduction
33. Abduction and anteversion to be read off the edges of the disk
34. Threaded hole for fixing cup positioner
35. Frame of Guide
36. Thread/implement fixing means
37. Surgical instrument
38. Laser pointer
39. Frame of pelvic positioner
40. Pad of pelvic positioner (to rest on operating table)
41. Operating table (plane)

The orientation device shown in FIG. 1A is a guide 2 and comprises a frame 35, a fixing means 11 which are adapted to be fixed to an acetabular prosthetic cup instrument 4 (see also FIGS. 5,6,7,9, 12 and 13), and a guide shaft 8 with pointers at its free end. Bubble levels 6, consisting of one right 9 and one left 10 indicators, are fixed to the fixing means 11. The bubble level orientation can be adapted (calibrated) by deformation of the bubble level support.

Figure 5:
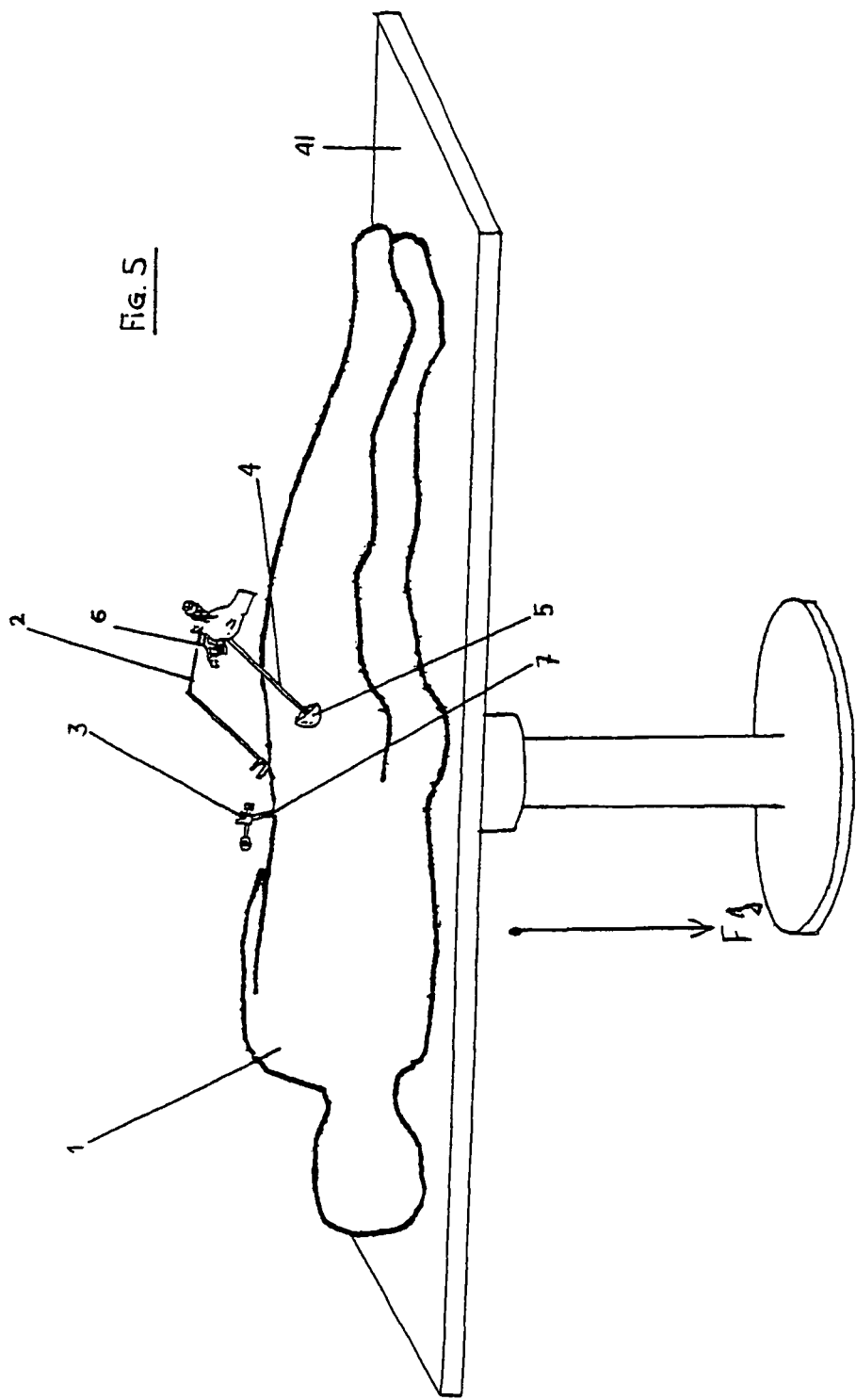
FIG. 5 shows the guide of FIG. 1 in use.
Figure 6:
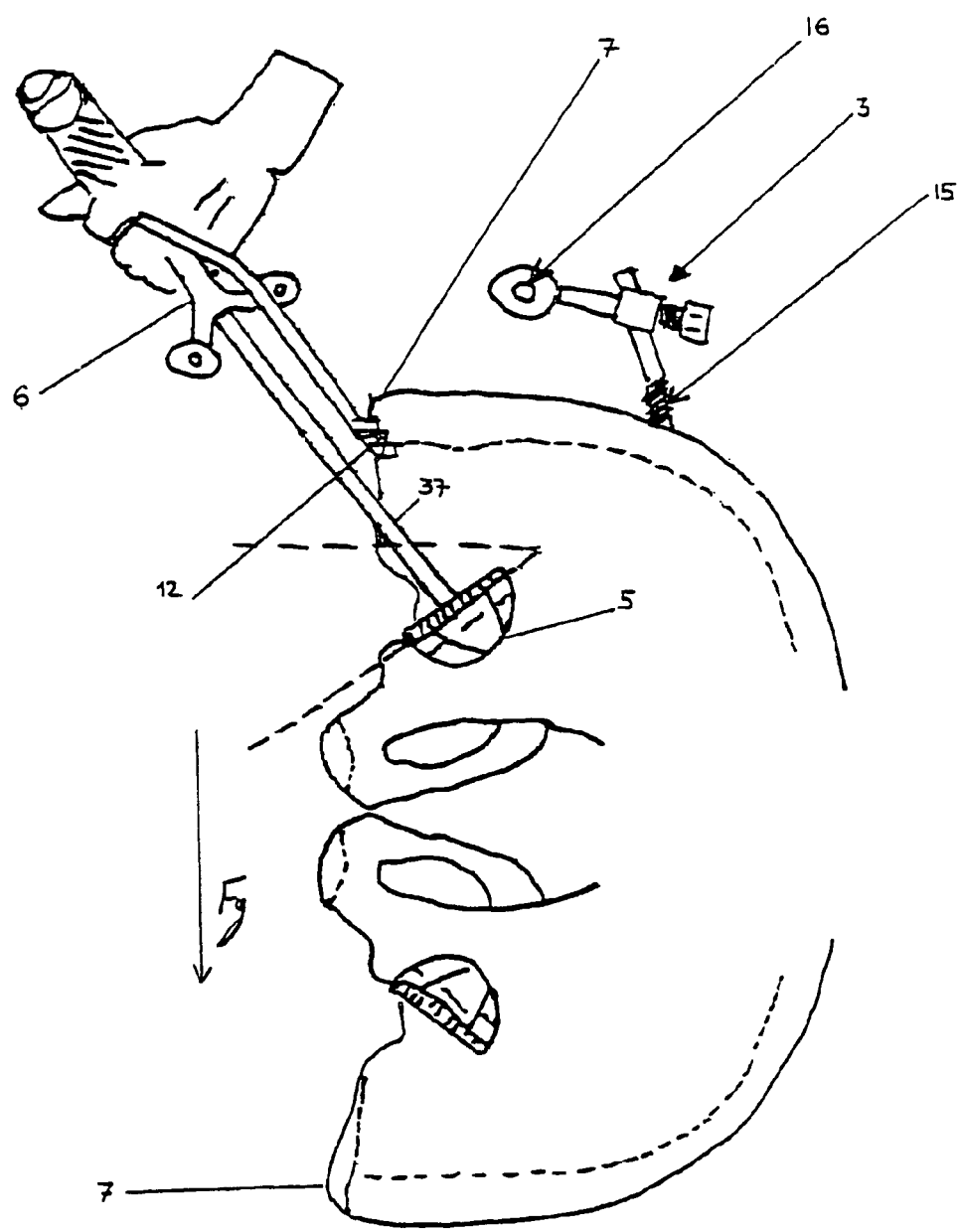
FIG. 6 is an enlarged view of the guide of FIG. 1 in use.
Figure 14:
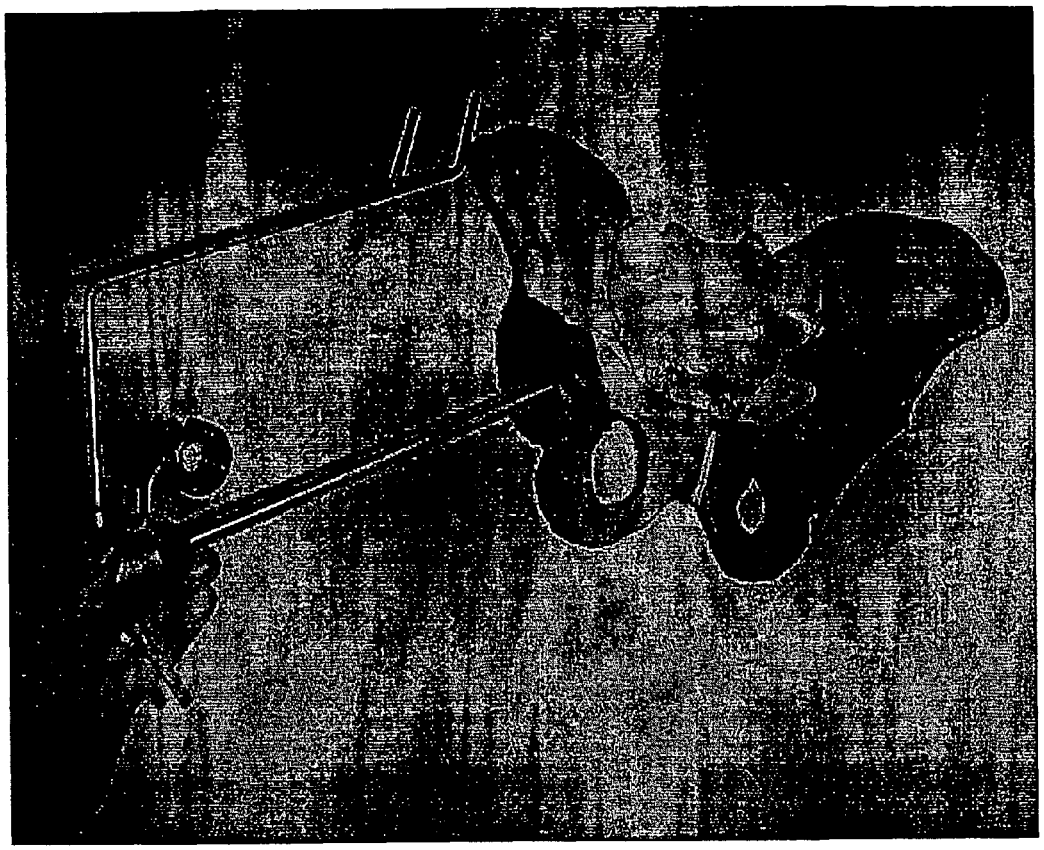
FIG. 14 illustrates the way to position the guide with respect to the ASIS.

The pointers 12 help to align the guide shaft 8 with the ASIS 7 (see FIGS. 5, 6 and 14).

Figure 1B:
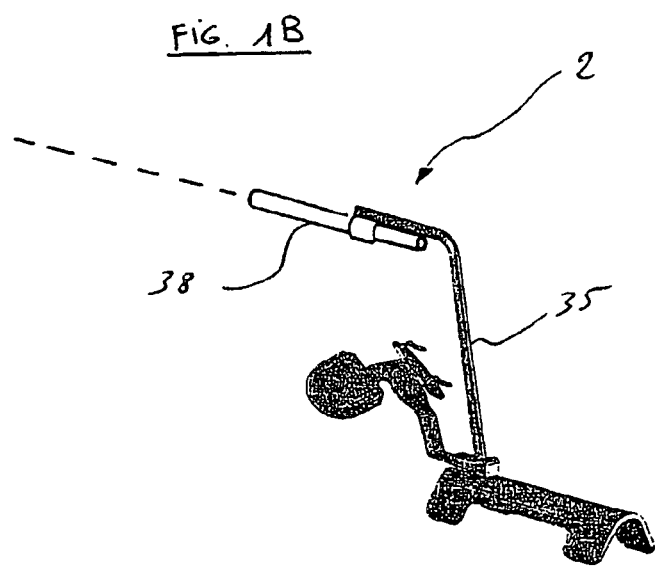
FIG. 1B shows an alternate embodiment of the guide, with a laser pointer.

Referring now to FIG. 1B, a laser pointer 38 is substituted for pointers 12. The laser pointer 38 produces a laser beam which the operator points at the ASIS 7.

Figure 3:
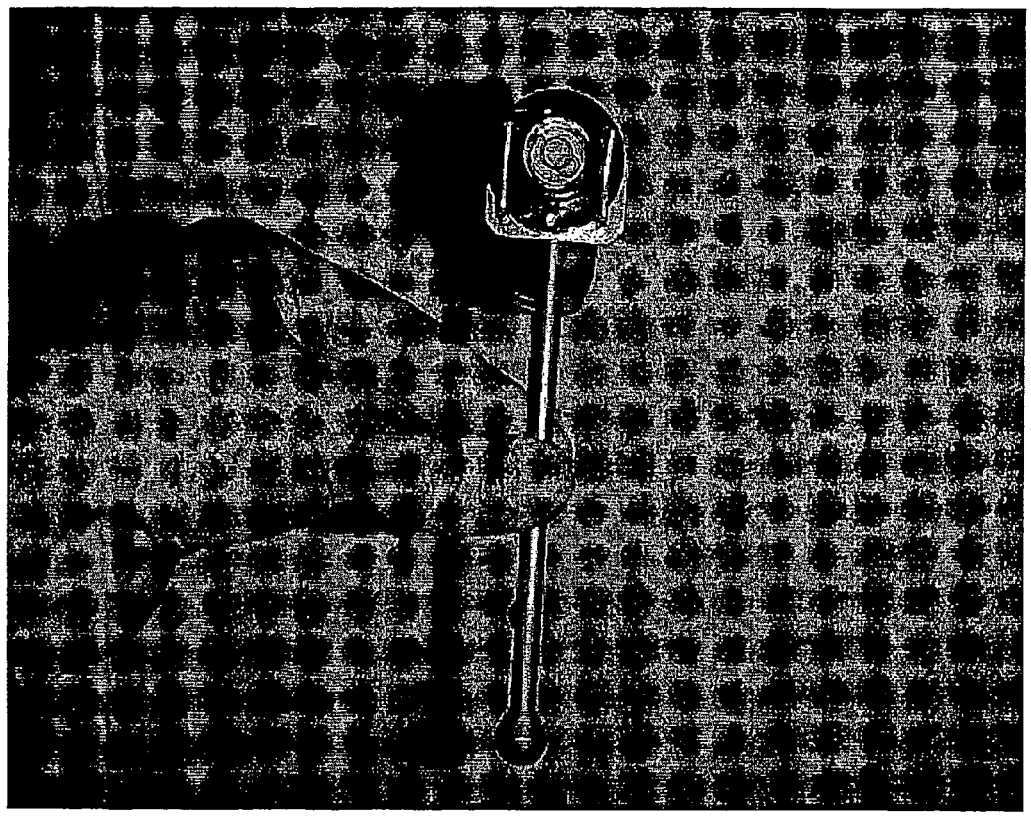
FIG. 3 shows the pelvic positioner of FIG. 2 from above with a bubble level.
Figure 4:
FIG. 4 shows the pelvic positioner of FIG. 2 being placed close to a pelvis.

FIGS. 2 to 4 show a pelvic positioner 17 made of frame 39 having an adjustable support 18 incorporating a two-dimensional bubble level 19 and two bars 20 having at their free end pelvic feelers 22. The bubble level 19 helps to position the pelvis in strict lateral decubitus using as a reference the antero superior iliac spines (ASIS) and the direction of the force of gravity Fg.

The bars 20 must come into contact with ASIS 7 through palpation with, for example, middle and annular fingers, which allows identification of the pelvic position. A pad 40 on an end thereof provides a reference surface which, when placed against the plane of the operating table 41 ensures perpendicular orientation therewith.

FIG. 5 shows a patient in strict lateral decubitus.

The correct orientation of the guide 2 is obtained when the bubble level 10 is at zero. The pelvic orientation is permanently checked with another embodiment of the invention, an orientation witness 3 (see also FIG. 6), made of bubble level 16 linked to a fixator 15 fixed to the iliac crest 13. The fixator 15 may be made of a "SHANZ" pin and clamp of a "HOFFMANN II"™ hand external fixator, allowing fixation to the iliac crest 13 via a Shanz Pin (commercially available).

The right 9 and left 10 indicators precisely identify the direction of the force of gravity Fg giving the adequate orientation in abduction and anteversion previously calibrated at manufacture or by the surgeon taking into account two points reference. Thanks to these two points, e.g. ASIS 7 and the instrument shaft free end, the flexion/extension of the pelvis the "Pitch" is taken into account.

FIG. 6 more clearly shows the orientation of the pelvis 13 in lateral decubitus. It represents an axial view showing anteversion of the cup 14.

Figure 7:
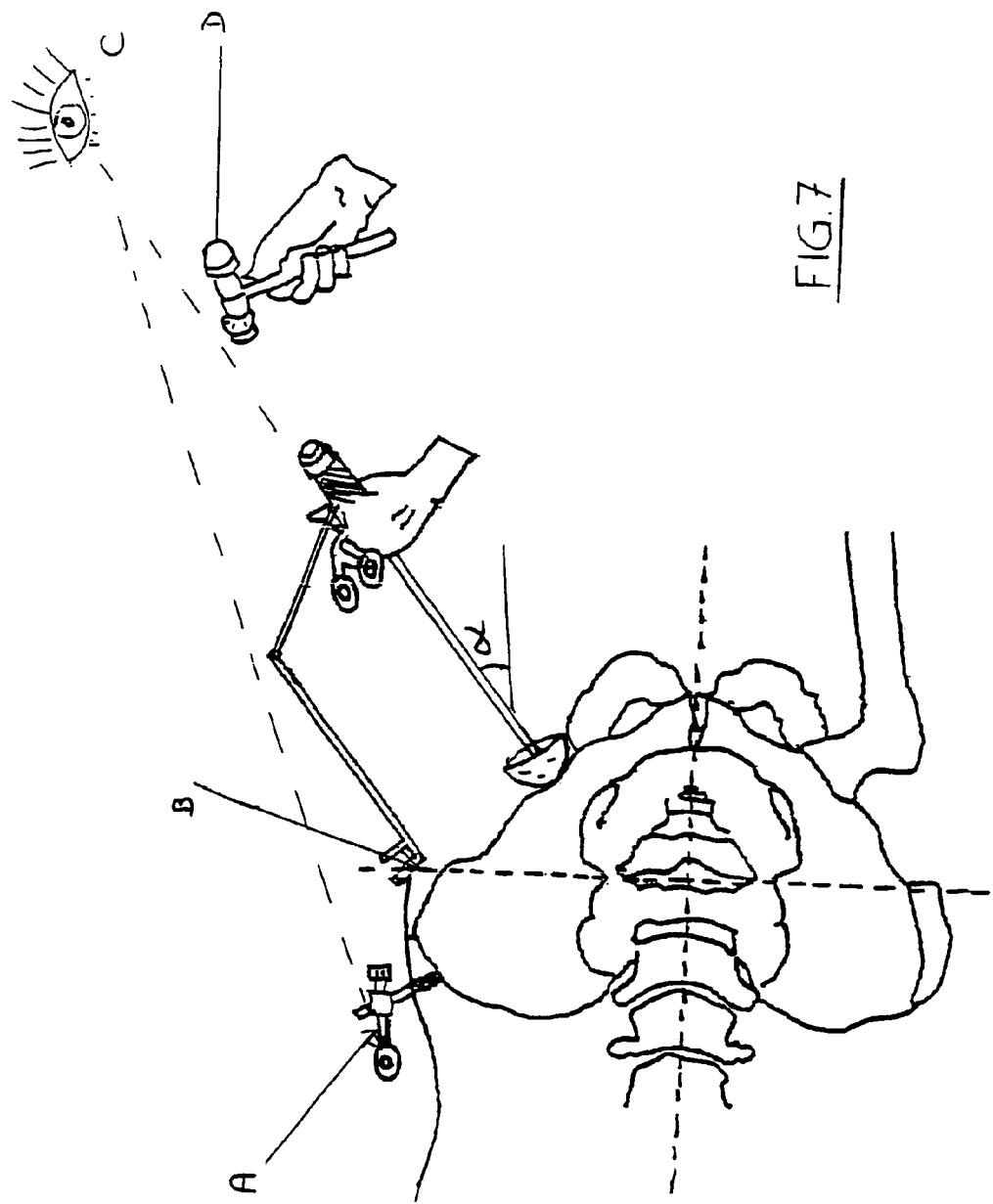
FIG. 7 illustrates the different operating actions when using the guide of FIG. 1.

FIG. 7 indicates the different operating steps when using the guide 2.

A: Control of the pelvic orientation in real time.
B: Alignment of the pointers 12 with the ASIS 7.
C: Permanent visualization of the pelvis 13 and implement 4, 37 orientation.
D: Impacting once desired orientation has been obtained.

Figure 8:
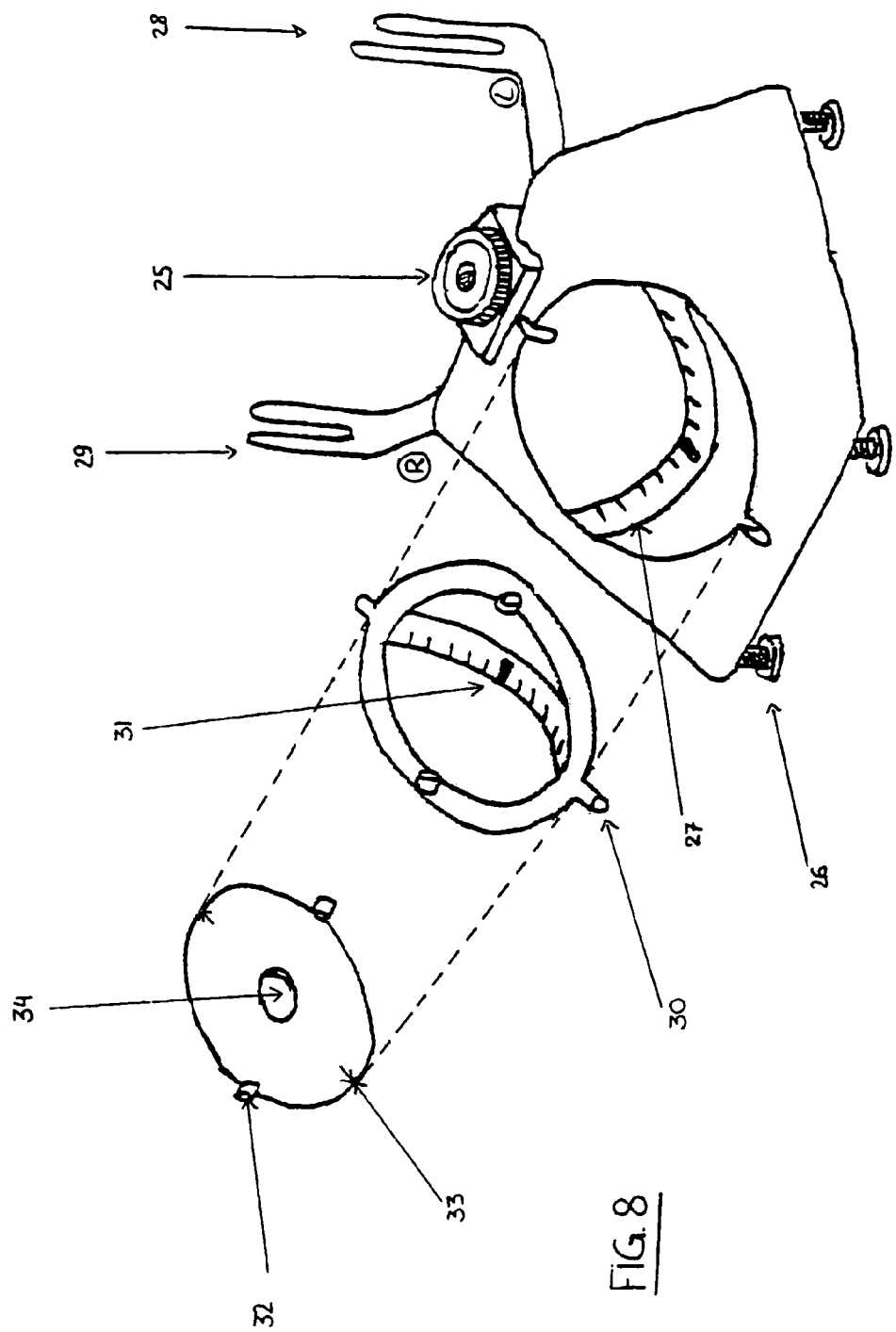
FIG. 8 is an exploded view of a calibrating apparatus.
Figure 9:
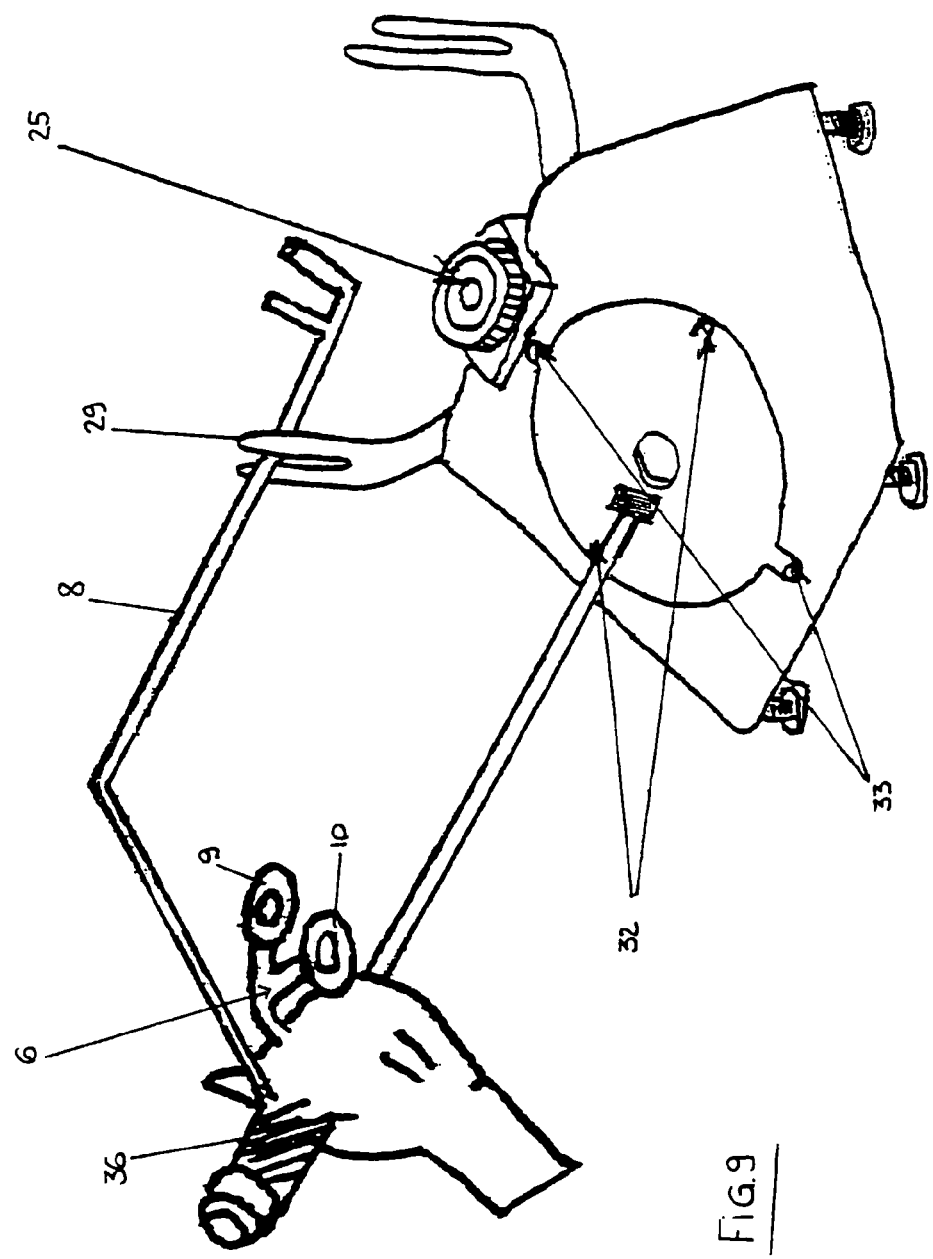
FIG. 9 shows the calibrating apparatus of FIG. 8 in use with the guide of FIG. 1.

The desired orientation of the guide 2 is obtained with the callibrating apparatus illustrated in FIGS. 8 and 9. The bubble level 6 can be bent (made of bendable material) centering the bubble and thus recording the desired orientation.

Desired anteversion 32 or "recorded" anteversion is read off these edges.

Desired abduction 33 or recorded abduction is read off these edges.

On the calibrating apparatus, the distance between the forks can be altered so as to calibrate for the specific angle of the patient (i.e. the angle between the HJC and the pubis at the ASIS). It should be noted at this point that this angle may change from 33 to 41 degrees from one patient to the other.

Figure 10:
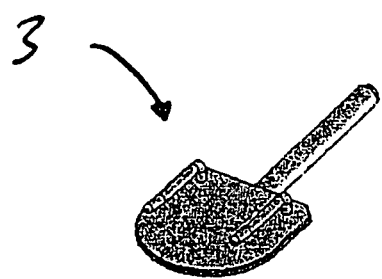
FIG. 10 shows a pelvic orientation witness without its bubble level.

FIG. 10 shows a pelvic orientation witness 3 made of a planar support and a shaft. The planar support has two flexible elements which are adapted to hold a bubble level in a similar way as shown on FIG. 3.

Figure 11:
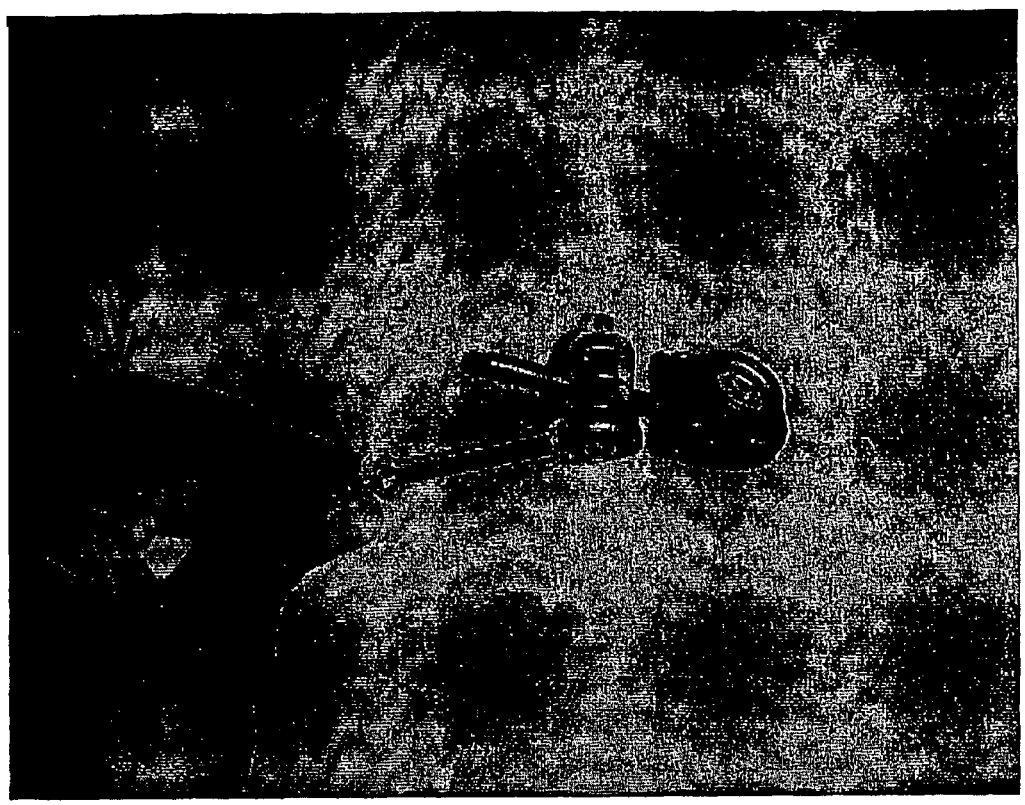
FIG. 11 shows a pelvic orientation witness linked to a pelvic fixator.
Figure 12:
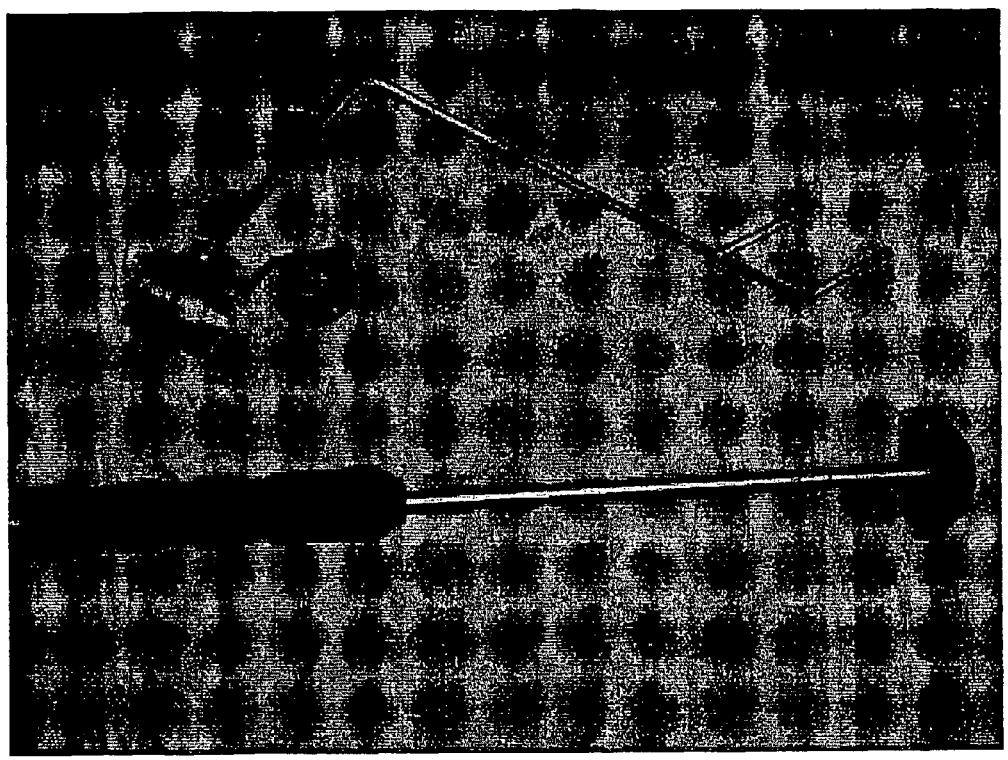
FIG. 12 shows a guide and an instrument separated from each other.
Figure 13:
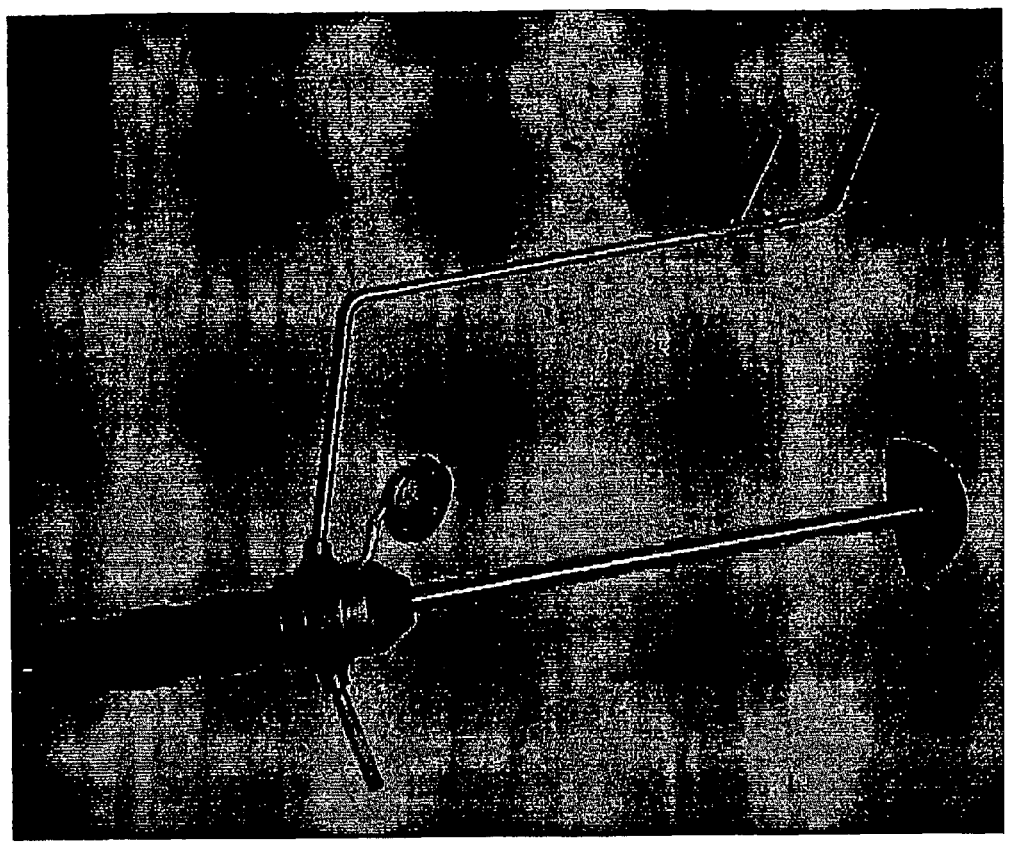
FIG. 13 shows the guide and the instrument of FIG. 12 fixed to each other.

The orientation witness 3 (see FIG. 11) is pivotally linked to a fixator 15 which has a free end adapted for being fixed to the pelvis.

Figure 15:
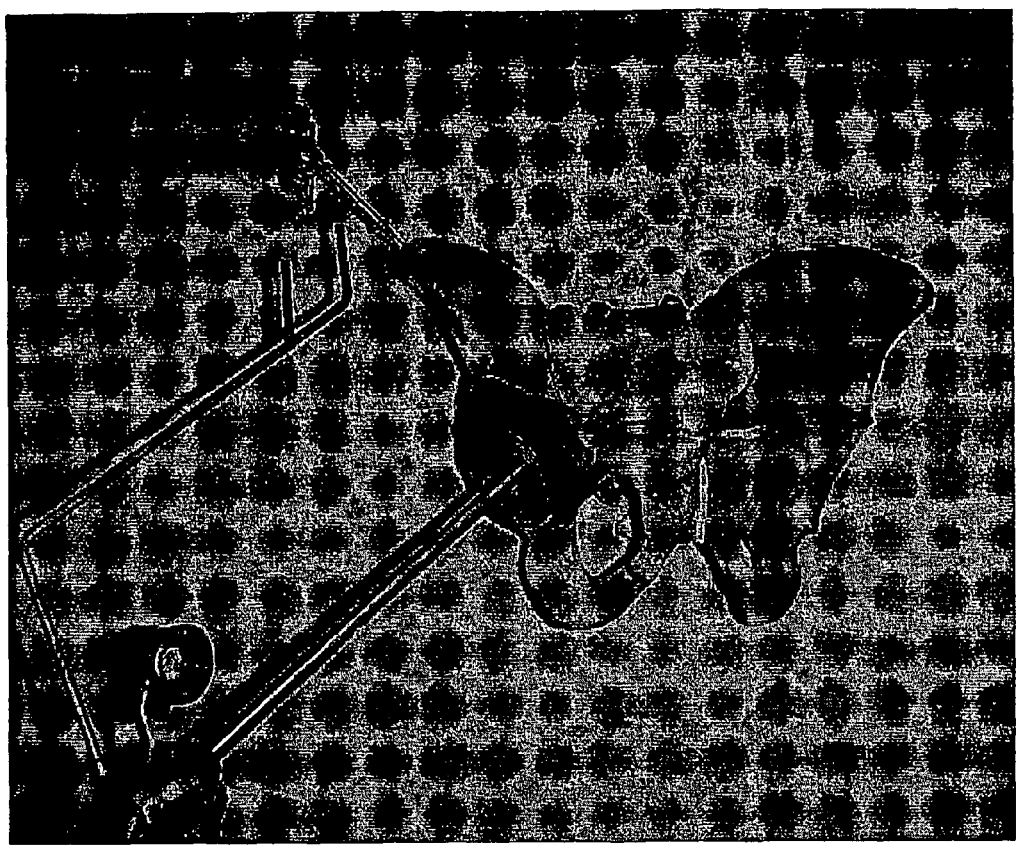
FIG. 15 shows the relation between the guide, instrument and the pelvic orientation witness.

In operation, the embodiment of the invention which is a guide which attaches to a surgical instrument, is used in the following manner:

1—Install the patient 1 in strict lateral decubitus and fix the pelvis 13 in the usual fashion with the pubic and sacral supports.
2—Control that the ASIS 7 are parallel to the direction of the force of gravity Fg with pelvic positioner 17 (see FIG. 4). This controls the initial position of the pelvis 13 in "Roll" and "Yaw".
3—Proceed to disinfection and draping of the extremity. Through a two centimeter skin incision over the iliac crest, implant a Shanz pin 15.
4—Using a clamp from a Hoffman II external hand fixator, set to zero the orientation witness or any other clamping device. The pin must be blocked to the iliac crest to void rotation. 3. These will allow resetting of the pelvis 13 to the initial desired position with respect to the direction of the force of gravity Fg at key intervals during surgery, such as acetabular reaming and cup impaction (see FIG. 14). This avoids the possibility of correct positioning with respect to direction of the force of gravity Fg but erroneous with respect to the pelvis 13.
5—Continue with an usual surgical technique until the last reaming. Check that the pelvis 13 is in the initial desired position by looking at the orientation witness 3 (see FIG. 15) and correct if necessary by moving the pelvis 13 until the bubble is set to zero.
6—For a factory pre calibrated guide, place the last reamer 37 inside the acetabulum, place the pointer 12 over the easily palpable ASIS 7, move the guide 2 until the bubble is centered identifying with precision the direction of the force of gravity Fg.
7—Run the reamer in that position to obtain a cavity in the precalibrated orientation (Abduction and Anteversion).
8—To place the final cup 14, adapt the guide 2 and the cup positioner 4, repeat step 5 and then 6.
9—To measure the cup 14 orientation in a patient, adapt the cup positioner 4 to the cup 14, check that the pelvis 13 is adequately oriented with the orientation witness 3 and correct if necessary. Align the pointer 12 with the ASIS 7 and bend the support of the bubble level 6 until the bubble is centered identifying with precision the direction of the force of gravity Fg.
10—Screw the cup positioner 4 and the guide 2 on to the calibrating apparatus 23.
11—Move both elements 4,2 of the instrument until the bubble is centered identifying the direction of the force of gravity Fg while placing the pointer 12 over one of the forks 28,29 that simulate the ASIS 7 location and read from the disc 27,31 the corresponding abduction and anteversion.

The present invention offers several advantages.

In a first advantage, enhanced accuracy and precision of acetabular cup orientation is attained, both abduction and anteversion of the cup by providing real time pelvic and acetabular cup orientation.

In another advantage, it allows precise reaming of the cavity in the desired orientation.

In another advantage, the invention helps control the desired orientation of the pelvis in strict lateral decubitus or strict dorsal decubitus hence controlling the pelvic position in the three planes at the time of cup insertion.

In another advantage, the invention provides ease of use without requiring the surgeon to look at the guide from a specific point of view. Seeing the bubble or bulls' eye level is enough to determine the orientation.

In another advantage, the invention is low cost and little training is required, making it available to surgeons even in developing countries.

In another advantage, the invention is useful in minimally invasive surgery techniques MIS.

In another advantage, no more time required than with existing techniques.

In still another advantage, the invention allows the surgeon to calibrate his instrument to the desired orientation (abduction and anteversion).

In still another advantage, the invention allows orientation of acetabular cups already in situ can be reliably measured with the guide.

In another advantage, the invention is adaptable to existing ancillary and current surgical techniques in dorsal decubitus, lateral decubitus, cemented, uncemented, anterolateral or posterolateral approaches.

Instead of using bubble levels, electronic devices identifying the direction of the force of gravity may be adapted to all the instruments mentioned.

Further, instead of pointing to a reference point on a patient, the invention can be adapted so as to point at a reference point associated with the patient, such as a point on a device which mounts on the patient (thereby, indirectly pointing at a point on a patient).

Further, in the present description, discussion about the prior art and detailed description of the invention are limited to the positioning of an acetabular prosthetic element. It should however be noted that the object of the invention and its claimed subject-matter are not limited to this specific use.

Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

The invention claimed is:

1. A medical guide for an acetabular prosthetic cup instrument, said guide comprising:
a shaft,
instrument fixing means for fixing said guide to a surgical instrument, and
a frame situated between said shaft and said instrument fixing means, wherein said guide for an acetabular prosthetic cup instrument further comprises:
pointing means situated at the shaft distal end,
orientation means, distinct from the shaft, which are adapted to define a reference plane, and wherein the orientation means are a dual-axis type,
wherein the orientation means are two bubble levels, and wherein said pointing means comprise a air of parallel shafts which are oriented at an angle with resect to the shaft direction.

2. The medical guide according to claim 1, wherein said orientation means are adjustable.

3. The medical guide according to claim 1, wherein the first bubble level is adapted for orientating an instrument fixed to said guide with respect to a right hip, and wherein the second bubble level is adapted for orientating said instrument with respect to a left hip.

4. The medical guide according to claim 1, wherein said instrument fixing means are adapted to allow a quick fixation or release of the guide to/from the instrument.

5. A combination of the medical guide according to claim 1 together with an acetabular prosthetic cup instrument comprising a shaft and with a handle at its proximal end and with a distal end adapted for receiving either a reamer or a cup positioner.

6. A combination of the medical guide according to claim 1 together with a pelvic positioner, said pelvic positioner comprising two arms with respective feelers and orientation means.

7. A combination of the medical guide according to claim 1 together with a pelvic orientation witness, said pelvic orientation witness comprising pelvic fixing means for fixing said pelvic orientation witness to the pelvis and orientation means.

8. A combination of the medical guide according to claim 1 together with an angle measuring device for measuring the angle between ASIS (Anterio Superior Iliac Spine) and HJC (Hip Joint Center).

9. A calibrating apparatus for calibrating a guide and an instrument as defined in claim 1, said calibrating apparatus comprising angle reproducing means for reproducing the angle between ASIS and HJC.

10. A medical guide for an acetabular prosthetic cup instrument, said guide comprising:
a shaft,
instrument fixing means for fixing said guide to a surgical instrument, and
a frame situated between said shaft and said instrument fixing means, wherein said guide for an acetabular prosthetic cup instrument further comprises:
pointing means situated at the shaft distal end,
orientation means, distinct from the shaft, which are adapted to define a reference plane, and wherein the orientation means are a dual-axis type, and
wherein the orientation means are an electronic device identifying the direction of the force of gravity, and
wherein said pointing means comprise a pair of parallel shafts which are oriented at an angle with respect to the shaft direction.

11. The medical guide according to claim 10, wherein said orientation means are adjustable.

12. The medical guide according to claim 10, wherein said instrument fixing means are adapted to allow a quick fixation or release of the guide to/from the instrument.

13. A combination of the medical guide according to claim 10 together with an acetabular prosthetic cup instrument comprising a shaft and with a handle at its proximal end and with a distal end adapted for receiving either a reamer or a cup positioner.

14. A combination of the medical guide according to claim 10 together with a pelvic positioner, said pelvic positioner comprising two arms with respective feelers and orientation means.

15. A combination of the medical guide according to claim 10 together with a pelvic orientation witness, said pelvic orientation witness comprising pelvic fixing means for fixing said pelvic orientation witness to the pelvis and orientation means.

16. A combination of the medical guide according to claim 10 together with an angle measuring device for measuring the angle between ASIS (Anterio Superior Iliac Spine) and HJC (Hip Joint Center).

17. A calibrating apparatus for calibrating a guide and an instrument as defined in claim 10, said calibrating apparatus comprising angle reproducing means for reproducing the angle between ASIS and HJC.

18. A medical guide for an acetabular prosthetic cup instrument, said guide comprising:
a shaft,
instrument fixing means for fixing said guide to a surgical instrument, and
a frame situated between said shaft and said instrument fixing means, wherein said guide for an acetabular prosthetic cup instrument further comprises:
pointing means situated at the shaft distal end,
orientation means, distinct from the shaft, which are adapted to define a reference plane, and wherein the orientation means are a dual-axis type,
wherein the orientation means are two bubble levels, and
wherein the first bubble level is adapted for orientating an instrument fixed to said guide with respect to a right hip, and wherein the second bubble level is adapted for orientating said instrument with respect to a left hip.

19. The medical guide according to claim 18, wherein said pointing means comprise a laser beam.

20. A medical guide for an acetabular prosthetic cup instrument, said guide comprising:
a shaft,
instrument fixing means for fixing said guide to a surgical instrument, and
a frame situated between said shaft and said instrument fixing means, wherein said guide for an acetabular prosthetic cup instrument further comprises:
pointing means situated at the shaft distal end,
orientation means, distinct from the shaft, which are adapted to define a reference plane, and wherein the orientation means are a dual-axis type, and
wherein the orientation means are an electronic device identifying the direction of the force of gravity,
and wherein the medical guide is combined with an acetabular prosthetic cup instrument comprising a shaft and with a handle at its proximal end and with a distal end adapted for receiving either a reamer or a cup positioner.

21. The medical guide according to claim 20, wherein said pointing means comprise a laser beam.

* * * * *